United States Patent [19]

Derfler et al.

[11] 4,312,854
[45] Jan. 26, 1982

[54] IMMUNOASSAY FOR THYROID STIMULATING HORMONE EMPLOYING FLORISIL ADSORBENT AS SEPARATING AGENT

[75] Inventors: Sara Derfler; Maksim Gur, both of Jerusalem, Israel; Daniel B. Wagner, Raleigh, N.C.

[73] Assignee: Ames-Yissum Ltd., Jerusalem, Israel

[21] Appl. No.: 75,059

[22] Filed: Sep. 12, 1979

[30] Foreign Application Priority Data

Sep. 13, 1978 [IL] Israel ................................ 55565

[51] Int. Cl.³ .................. G01N 33/48; G01T 1/00; B65D 71/00
[52] U.S. Cl. .................................. 424/1; 23/230 B; 23/230.3; 422/61; 424/12
[58] Field of Search .................... 424/1, 12, 1.5; 23/230 B, 230.3, 230.6; 422/61

[56] References Cited

U.S. PATENT DOCUMENTS

| | | | |
|---|---|---|---|
| 3,666,854 | 5/1972 | Eisentraut | 424/1 |
| 3,743,482 | 7/1973 | Eisentraut | 23/230 B |
| 3,775,615 | 11/1973 | Eisentraut | 23/230 B |
| 3,776,698 | 12/1973 | Eisentraut | 23/230 B |
| 4,088,746 | 5/1978 | Blakemore et al. | 23/230 B |

*Primary Examiner*—Benjamin R. Padgett
*Assistant Examiner*—Christine M. Nucker
*Attorney, Agent, or Firm*—Andrew L. Klawitter

[57] ABSTRACT

An improved immunoassay method for determining thyroid stimulating hormone (TSH) in a liquid sample wherein the bound- and free-species of the labelled, preferably radio-labelled, TSH are separated by contacting the liquid reaction mixture with Florisil adsorbent which selectively adsorbs free TSH and physically separating the adsorbent from the liquid mixture. The Florisil adsorbent is preferably contained in a column form. A test kit for performing the improved method is also provided. The assay is more simple and less time consuming than the prior art techniques.

17 Claims, No Drawings

IMMUNOASSAY FOR THYROID STIMULATING HORMONE EMPLOYING FLORISIL ADSORBENT AS SEPARATING AGENT

BACKGROUND OF THE INVENTION

1. Field of the Invention

The present invention concerns the quantitative determination of Thyroid Stimulating Hormone (hereinafter "TSH") in aqueous solutions. More particularly, the present invention provides a method and a kit for the determination of the concentration of TSH in body liquids, particularly in serum, by radioimmunoassay techniques.

TSH is a glycoprotein hormone secreted by the anterior pituitary gland and is the principal regulator of thyroid gland activity. This glycoprotein has a molecular weight of 28,000 and can be dissociated into two dissimilar sub-units of equal size, commonly designated as $\alpha$ and $\beta$-types, which are linked to each other by non-covalent bonds and which differ from each other in their amino acid composition and sequence and in their carbohydrate composition. The subunit is similar in its amino acid composition to the $\alpha$ sub-units of luteinizing hormone, follicle-stimulating hormone and human chorionic gonadotropin, whereas the $\beta$ sub-unit of TSH is of a distinct character and is responsible for the biological and immunological specifity of this hormone. The primary functions of TSH are to stimulate thyroidal iodide metabolism and thyroid hormone synthesis and release by the thyroid gland. TSH also stimulates several other metabolic processes in the thyroid gland, including cyclic AMP generation, glucose oxidation, oxygen consumption and the synthesis of proteins and phospholipids.

TSH assay is an important diagnostic tool for diagnosing and monitoring the treatment of various disturbances of the thyroid gland function, e.g., primary hyperthyroidism. Owing to the inadequate sensitivity of current TSH radioimmunoassay methods, this assay cannot be used for the determination of lower-than-normal serum TSH levels, such as occur in hyperthyroidism.

2. Description of the Prior Art

Practically all the known methods for the determination of TSH in serum utilize the so-called "double antibody" radioimmunoassay technique with $^{125}$I-labelled TSH. Radioimmunoassay methods, in general, are based on the competition between a specific native antigen, the amount of which is to be determined in a sample, and a known amount of the same antigen in radioactively labelled form, for a limited number of available binding sites on an antibody which is specific towards the antigen under assay. Thus, in a system consisting of an unknown amount of unlabelled native antigen, a known amount of a radioactively labelled antigen and a limited known amount of antibody, the greater the concentration of unlabelled native antigen from the sample, the less the labelled antigen will be bound by the antibody. By separating the antigen-antibody complex (the "bound" species) from the remaining free antigen (both labelled and unlabelled—the "free" species) and measuring the radioactivity in one and/or the other fraction, it becomes possible to establish an assay system for measuring the unknown level of unlabelled antigen in the patient's sample. As a rule, a standard calibration curve for the specific system is established by a series of assays of standard samples with varying known amounts of unlabelled antigen and this curve is then used to determine an unknown concentration of the antigen in a sample.

There are many procedures for separating the antigen-antibody complex from the free unbound antigen, amongst which chromatoelectrophoresis, ascending paper-wick chromatography, precipitation by salts, organic materials or solvents, selective adsorption on various so-called "immunsorbents," either in suspension or on chromatographic columns, and ion exchange techniques may be mentioned as examples of such procedures. U.S. patent application Ser. No. 852,105, filed Nov. 16, 1977 and assigned to the instant assignee, is incorporated herein by reference and describes in more detail such prior art techniques for separating the bound- and free-species of the labelled antigen.

The separation of the antigen-antibody complex from the free unbound antigen is particularly difficult where the antigen is a molecule of comparatively high molecular weight (as contrasted to the relatively small and simple haptens), approaching that of the protein molecule of the antibody. Examples of such high molecular weight antigens are the various peptide hormones including the glycoprotein TSH with which the present invention is concerned. One of the separation procedures used in known radioimmunoassay methods of peptide hormones an in most, if not all, TSH radioimmunoassay tests, is the "double antibody" technique. By this technique the primary antigen-antibody complex is precipitated from its solutions as a secondary complex formed with a second antibody that was raised against the first antibody. For example, if the first antibody was raised in a rabbit against a specific antigen, then the second antibody may be an antiserum raised in goats and is specific against the first antibody or, less specifically, against rabbit gammaglobulin. This method is applicable to practically any radioimmunoassay test and results in complete separation of the antigen-antibody complex from the free native antigen, but it has the disadvantages of being comparatively costly and complicated [e.g., an additional incubation period is necessary for the formation of the antigen-(first antibody)-(second antibody) complex].

It is the object of the present invention to provide a simple, inexpensive and reliable method for the quantitative determination of TSH in aqueous solutions, particularly in serum samples.

SUMMARY OF THE INVENTION

In accordance with the present invention, it has surprisingly been found that TSH-antibody complex can be effectively separated from free native TSH (both radioactively labelled and unlabelled) by the selective adsorption of the free unbound TSH on Florisil ® adsorbent available from Floridin Company, Warren, PA.

Florisil adsorbent is a hard, granular, porous, synthetically activated magnesium silicate prepared according to the method of U.S. Pat. No. 2,393,625 (expressly incorporated herein by reference) and having a typical composition of MgO 15.5%; $SiO_2$ 84%; $Na_2SO_4$ 0.5%. Florisil adsorbent is commercially available in various mesh sizes and has found extensive use as an adsorbent in preparative and analytical chromatography, e.g., in the isolation of steroids, sex hormones, antibiotics, alkaloids, the separation of lipids, assay of vitamins and in thin layer chromatography. Despite this wide use in various applications of chromatography, the only known use of Florisil adsorbent in radioimmunoassay separations is in steroid radioimmunoassay and, even there, it has been used as a suspension in the incubation solution rather than in a chromatographic column [cf. Dicztalusy, E. (Ed.), *Steroid Assay by Protein Binding*, *Acta Endocrinol.* (KbH) (suppl) 147, 1970].

It is of interest to note that there has been comparatively little progress recently in the use in radioimmunoassay of any of the inorganic adsorbents in general, such as talc, silica gel and Fuller's earth, and that in the last six or seven years, there has been almost no mention of this type of separation in the literature. It was thus entirely unexpected to find, in accordance with the present invention, that Florisil adsorbent can be very effectively used in TSH radioimmunoassay by virtue of the fact that it selectively adsorbs the free unbound TSH from the incubation mixture while leaving the TSH-antibody complex practically unadsorbed.

The present invention accordingly provides an improved immunoassay method for determining thyroid stimulating hormone in a liquid sample, (a) wherein said liquid sample is combined with a label-incorporated form (usually a radiolabelled form, e.g., with $^{125}I$) of thyroid stimulating hormone and an antibody to thyroid stimulating hormone to form a liquid mixture containing bount-species of said labelled thyroid stimulating hormone wherein such is bound by said antibody and a free-species of said labelled thyroid stimulating hormone wherein such is not bound by said antibody, (b) wherein said bound- and free-species are physically separated, and (c) wherein the amount of said label is measured in one of said separated species as a function of the presence or amount of thyroid stimulating hormone in said sample.

The improvement comprises accomplishing said separation of said bound- and free-species by contacting said liquid mixture with Florisil adsorbent whereby substantially all of said free-species is adsorbed thereto with substantially no adsorption of said bound-species and physically separating from said liquid mixture the Florisil adsorbent having said free-species adsorbed thereto.

Further, the present invention provides a test kit for use in an immunoassay method for determining thyroid stimulating hormone in a liquid sample, comprising, in a packaged combination, (a) one or more containers holding the label-incorporated form of thyroid stimulating hormone, and the antibody to thyroid stimulating hormone, and (b) a container holding a quantity of Florisil adsorbent, e.g., in a column form.

In accordance with a preferred embodiment of the invention the Florisil adsorbent is contained in a tube or column, of the type conventionally used for adsorption chromatography either of the conventional descending type or an ascending type (cf., e.g., the aforesaid U.S. patent application Ser. No. 852,105). In the conventional descending mode, the tube or column is provided at its bottom end with retainer means pervious to the liquid reaction mixture, usually an aqueous liquid, and serving as support for the Florisil adsorbent. Similar retainer means are advantageously provided also on the top of the Florisil adsorbent column in the tube. In accordance with this embodiment, the liquid reaction mixture is applied to the top of the Florisil adsorbent in the tube or column and allowed to flow downwardly through the adsorbent. The adsorbent is then washed or eluted with water or with a suitable aqueous buffer solution, in order to free the Florisil adsorbent from any residual amounts of the reaction mixture containing the TSH-antibody complex which is not adsorbed, or only weakly adsorbed, by the adsorbent in the column. In accordance with this embodiment it is preferable to wash the Florisil adsorbent in the tube, before the reaction mixture is applied thereto, with a slightly alkaline aqueous buffer solution, e.g., the "TSH-buffer" of pH 7.8 described hereinafter in the Examples.

In accordance with a modification of the above described embodiment, a tube or column filled with Florisil adsorbent as described above, may be employed in the so-called "ascending chromatography" technique which is described in detail in the aforesaid U.S. patent application Ser. No. 852,105. In accordance with this technique the bottom end (intake tip) of a tube or column filled with Florisil adsorbent is vertically dipped into the reaction mixture contained in a suitable vessel, preferably a test tube, whereby the reaction mixture ascends into the adsorbent by capillary forces and is adsorbed by the Florisil adsorbent in the column. The adsorbent is then washed in the same manner by allowing an amount of water or aqueous buffer solution to ascend into the column through its intake tip. In this modification, the free TSH, both native and the labelled form, are preferentially adsorbed and retained in the intake tip region of the column, whereas the residual reaction mixture including the non-adsorbed TSH-antibody complex migrates upwardly in the Florisil adsorbent column. The two components thus become separated along the column and their distance apart is sufficient to enable a selective determination of the radioactivity of the intake tip region of the column.

Various types of labels may be used according to the state of the art. Preferably radioactive labels are used. The radioactively labelled TSH commonly used in TSH-radioimmunoassay is TSH labelled with $^{125}I$ (hereinafter "$^{125}I$-TSH"). It has been found that this species of labelled TSH exhibits a markedly increased affinity to TSH antibody as compared to native (i.e., unlabelled) TSH. Thus, if the radioimmunoassay reaction mixture is prepared in the conventional manner, namely by mixing both native TSH and $^{125}I$-TSH with the specific TSH antibody followed by incubation of this mixture, the $^{125}I$-TSH would strongly outmatch the native TSH in the competition for the limited number of available binding sites on the TSH specific antibody and as a result all these binding sites would be occupied by $^{125}I$-TSH bound thereto by complex formation, whereas practically no native TSH would enter into complex formation with the antibody. This situation would clearly render the immunoassay technique using $^{125}I$-TSH as the radioactively labelled species practically useless.

The aforementioned difficulties are avoided in accordance with a preferred embodiment of the present invention which provides a method for the quantitative determination of TSH in an aqueous liquid sample comprising the steps of:

combining said aqueous liquid sample with a specific TSH antibody;

incubating said reaction mixture to cause a reaction between the TSH and said TSH antibody so that at least a part of the TSH forms a (TSH-antibody) complex;

adding to the reaction mixture a known quantity of $^{125}I$-TSH;

incubating said reaction mixture to cause the $^{125}I$-TSH to react with said TSH antibody and/or with said (TSH-antibody) complex so that a part of the $^{125}$I-TSH forms a ($^{125}$I-TSH-antibody) complex;

contacting the resulting reaction mixture with Florisil adsorbent whereby the free TSH and the free $^{125}$I-TSH are preferentially adsorbed on the Florisil adsorbent;

separating the Florisil adsorbent from the aqueous phase containing said (TSH-antibody) complex and said ($^{125}$I-TSH-antibody) complex;

washing the Florisil adsorbent with water or an aqueous buffer solution; and measuring the radioactivity of either the washed Florisil adsorbent or said aqueous phase combined with the water or said buffer solution washings.

In accordance with this embodiment it is preferable to use for the washing (or elution) of the Florisil adsorbent an aqueous buffer solution having a pH less than 7.0, preferably between 4.0 and 6.0, in order to minimize the so-called "leakage" of the free $^{125}$I-TSH from the Florisil adsorbent in the course of the washing step.

It has also been found that improved results are obtained when the selectivity of the TSH antibody towards TSH is increased by including in the aqueous reaction mixture another glycoprotein, e.g., human chronionic gonadotropin (HCG), and/or when the antigen-binding capacity of the antibody is increased by adding to the reaction mixture a strong chelating agent for heavy metals, such as ethylenediamine tetraacetic acid (EDTA).

In order to determine the amount of TSH in a sample, e.g., in a patient's serum, a standard calibration curve is used as a rule, as explained above. Such a calibration curve is obtained by plotting the results of radioactivity measurements of a series of assays with standard samples including known amounts of native TSH within a certain range of concentrations, carried out under identical conditions as the assay of the unknown sample.

In accordance with the above procedure, it is sufficient to measure, in the assays of both the unknown and the standard samples, either the radioactivity of the free, unbound radioactively labelled TSH adsorbed on the Florisil adsorbent or the radioactivity of the labelled TSH which is bound by the antibody and is contained in the aqueous phase. This is based on the fact that the total radioactivity of the initial aqueous reaction mixture is determined, in principle, by the constant, predetermined amount of radioactively labelled TSH used for the preparation of that reaction mixture. However, in order to avoid one source of inaccuracy arising from imprecise dispending of the stock solution containing the radioactively labelled TSH, it may be preferable to establish the total radioactivity in each test experimentally ("initial count").

From the total radioactivity (initial count) and the radioactivity measured after the separation of the Florisil adsorbent from the aqueous phase (final count) the percent retention is calculated. Where the final count is obtained by measuring the radioactivity of the radioactively labelled TSH adsorbed on the Florisil adsorbent (or at the intake tip region of an "ascending chromatography" column packed with Florisil adsorbent), the percent retention is calculated as follows:

$$\% \text{ retention} = \frac{\text{final count}}{\text{initial count}} \times 100.$$

The "initial count" may alternatively be established by means of a parallel reference-assay, differing from the above defined process according to the invention in that the initial aqueous reaction mixture includes no native TSH and no TSH antibody, but contains instead corresponding volumes of serum (e.g., chicken serum) and buffer solution, respectively. This reaction mixture is submitted to the identical procedure as the actual radioimmunoassays, whereby the entire amount of radioactively labelled TSH in the initial reaction mixture is adsorbed by the Florisil adsorbent, since there is present no TSH anbibody which might bind a part of the radioactively labelled TSH by forming a complex therewith. The "initial count" is thus obtained by measuring the radioactivity of the Florisil adsorbent after it is separated from the aqueous phase and washed. The percent retention can be calculated in accordance with the above formula.

In another aspect the present invention provides, for the performance of the method of the invention, a test kit comprising packaged labelled (preferably radiolabelled) TSH, packaged TSH antibody, and the Florisil adsorbent. The kit may optionally also include packaged native TSH which is used for the establishment of a standard curve, as explained above. Further optional components of the kit are one or more packaged buffer solutions, for washing the Florisil adsorbent before the immunoassay reaction mixture is applied thereto and/or for the elution of the column (if used) after the reaction mixture has passed therethrough.

The invention is further illustrated in the following Example without being limited thereto.

EXAMPLE

The buffers used in this test were:

(1) Phosphate buffer, pH 7.8 (hereinafter "TSH-buffer"), prepared by dissolving 0,325 gram (g) of Na$_2$HPO$_4$, 0.30 g of NaH$_2$PO$_4$, 0.25 g of NaN$_3$ and 2.91 g of NaCl in 250 milliters (ml) of water.

(2) Citrate buffer, pH 5.0, prepared by dissolving 14.40 g of anhydrous citric acid, 47.70 g of sodium biphosphate, 2.70 ml of an aqueous 37% formaldehyde solution and 10.0 g of bovine serum albumin in one liter of water.

The following reagents were added to a polystyrene test tube having a length of about 10 centimeters (cm) and an inner diameter of about 1.2 cm:

(1) 500 microliters ($\mu$l) TSH standard (diluted with chicken serum) or a clinical serum sample;

(2) 100 $\mu$l of a solution of human chorionic gonadotropin (HCG) and ethylenediamine tetraacetic acid (EDTA) in TSH buffer;

(3) 100 $\mu$l anti-TSH antiserum diluted with TSH buffer.

The test tube was gently swirled in order to ensure thorough mixing of the reagents and the mixture was allowed to incubate for 17 hours at 25° C.

100 $\mu$l of $^{125}$I-TSH in water containing 2% BSA [about 17 thousand counts per minute (kcpm)] were then added to the mixture in the test tube. The test tube was again gently shaken in order to mix the reagents throughly, and allowed to incubate for 5 hours at 25° C.

A column was prepared by filling a polyethylene tube, provided at its bottom with a porous polyethylene retainer disc, with Florisil adsorbent 100–200 mesh, to a height of 2.5 cm above the disc, washing the column with TSH-buffer, allowing the Florisil adsorbent to settle and inserting a second polyethylene retainer disc into the top of the column. The column was then washed with TSH buffer containing 1% of bovine serum albumin (BSA).

750 μl of the incubated reaction mixture were transferred to the top of the above described column and allowed to penetrate into the Florisil adsorbent. The column was eluted with 2 ml of citrate buffer pH 5.0.

The radioactivity of the column was then determined with a gamma radiation counter and the "percent retention" calculated using the equation:

$$\% \text{ retention} = \frac{\text{final count}}{\text{initial count}} \times 100$$

where the "initial count" is determined as follows:
The following reagents were added to a test tube:
(1) 500 μl chicken serum
(2) 100 μl $^{125}$I-TSH
(3) 100 μl of a solution of HCG and EDTA in TSH buffer as described above
(4) 100 μl of TSH buffer.

The test tube is gently shaken in order to ensure thorough mixing of the reagents and 750 μl of the mixture are transferred to the top of a Florisil adsorbent column, prepared as described above, and allowed to penetrate into the Florisil adsorbent. The column is then eluted with 2 ml of citrate buffer pH 5.0, and the radioactivity of the column measured with the gamma radiation counter.

A standard curve was obtained by plotting the percent retention values against the corresponding concentrations of the TSH standards.

Unknown amounts of TSH in serum, can be determined in accordance with the above procedure with the aid of the standard curve. Using this standard curve clinical samples of human sera (with "low-normal" and "high" TSH values) were tested by the above described procedure, each in "N" number of replicates. The following results were obtained:

| Mean Value | N | C.V. %* |
|---|---|---|
| 1.5 μU/ml | 21 | 11.4 |
| 1.7 μU/ml | 20 | 7.0 |
| 1.67 μU/ml | 17 | 6.5 |
| 14.5 μU/ml | 19 | 11.8 |

*Coefficient of variation.

The "means values" were found to be in good agreement with the values obtained by other, conventional TSH test procedures.

When samples from the same incubation mixture were separated on 17 identical Florisil adsorbent columns, the coefficient of variation of the "mean values" obtained was as low as 4.3%.

We claim:
1. In an immunoassay method for determining thyroid stimulating hormone in a liquid sample,
   (a) wherein said liquid sample is combined with a label-incorporated form of thyroid stimulating hormone and an antibody to thyroid stimulating hormone to form a liquid mixture containing a bound-species of said labelled thyroid stimulating hormone wherein such is bound by said antibody and a free-species of said labelled thyroid stimulating hormone wherein such is not bound by said antibody,
   (b) wherein said bound- and free-species are physically separated, and
   (c) wherein the amount of said label is measured in one of said separated species as a function of the presence or amount of thyroid stimulating hormone in said sample,
the improvement which comprises accomplishing said separation of said bound- and free-species by contacting said liquid mixture with an adsorbent comprised of granular, porous, synthetically activated magnesium silicate, whereby substantially all of said free-species is adsorbed thereto with substantially no adsorption of said bound-species and physically separating from said liquid mixture the adsorbent having said free-species adsorbed thereto.

2. The method of claim 1 wherein said labelled thyroid stimulating hormone is radioactively labelled.

3. The method of claim 2 wherein said labelled thyroid stimulating hormone is labelled with $^{125}$I.

4. The method of claim 1 wherein the physically separated adsorbent having said free-species adsorbed thereto is washed and thereafter said label is measured either on said adsorbent or in the combined volume of said liquid mixture and the washings from said wash step.

5. The method of claim 5 wherein said wash step is accomplished with water or a buffer solution.

6. The method of claim 1 wherein said adsorbent is contained in a column and said separation of said bound- and free-species is accomplished by passing said liquid mixture through said column.

7. The method of claim 6 wherein the effluent from said passage through the column is collected, said column is washed by passing an aqueous liquid therethrough, the resulting wash effluent is collected, and said label is measured either in the column or in the combined effluents.

8. The method of claim 7 wherein said labelled thyroid stimulating hormone is radioactively labelled.

9. A radioimmunoassay method for the quantitative determination of thyroid stimulating hormone (TSH) in an aqueous liquid sample, comprising the steps of:
   (a) combining said aqueous liquid sample with a specific TSH antibody;
   (b) incubating said reaction mixture to cause a reaction between the TSH and said TSH antibody so that at least a part of the TSH forms a (TSH-antibody) complex;
   (c) adding to the reaction mixture a known quantity of radiolabelled TSH;
   (d) incubating said reaction mixture to cause the radiolabelled TSH to react with said TSH antibody and/or with said (TSH-antibody) complex so that a part of the radiolabelled TSH forms a (radiolabelled TSH-antibody) complex;
   (e) contacting the resulting reaction mixture with an adsorbent comprised of granular, porous, synthetically activated magnesium silicate, whereby the free TSH and the free radiolabelled TSH are preferentially adsorbed on the adsorbent;
   (f) separating the adsorbent from the aqueous phase containing said (TSH-antibody) complex and said (radiolabelled TSH-antibody) complex;
   (g) washing the adsorbent with water or an aqueous buffer solution; and
   (h) measuring the radioactivity of either the washed adsorbent or said aqueous phase combined with the water or said buffer solution washings.

10. The method of claim 9 wherein said labelled thyroid stimulating hormone is radioactively labelled.

11. The method of claim 10 wherein said labelled thyroid stimulating hormone is labelled with $^{125}$I.

12. A test kit for use in an immunoassay method for determining thyroid stimulating hormone in a liquid sample, comprising, in a packaged combination,
   (a) one or more containers holding a label-incorporated form of thyroid stimulating hormone and an antibody to thyroid stimulating hormone, and
   (b) a container holding a quantity of an adsorbent comprised of granular, porous, synthetically activated magnesium silicate.

13. The kit of claim 12 wherein said labelled thyroid stimulating hormone is radioactively labelled.

14. The kit of claim 13 wherein said labelled thyroid stimulating hormone is labelled with $^{125}$I.

15. The kit of claim 12 wherein said quantity of adsorbent is contained in a column.

16. A method for separating free thyroid stimulating hormone from thyroid stimulating hormone bound to an antibody thereto in a liquid medium, comprising the steps of contacting said liquid medium with an adsorbent comprised of granular, porous, synthetically activated magnesium silicate, whereby substantially all of said free thyroid stimulating hormone is adsorbed thereto with substantially no adsorption of said antibody-bound thyroid stimulating hormone, and physically separating the adsorbent said free thyroid stimulating hormone adsorbed thereto from said liquid medium.

17. The method of claim 16 wherein said adsorbent is contained in a column and said separation is accomplished by passing said liquid medium through said column and collecting the effluent.

* * * * *